(12) United States Patent
Rubinov et al.

(10) Patent No.: US 11,819,479 B2
(45) Date of Patent: Nov. 21, 2023

(54) COMPOSITIONS FOR THE TREATMENT OF BLEPHARITIS

(71) Applicant: THREE-R THERAPEUTICS LTD., Ein Vered (IL)

(72) Inventors: Michael Rubinov, Ein Vered (IL); Greg Rubin, Calabasas, CA (US)

(73) Assignee: THREE-R THERAPEUTICS LTD., Ein Vered (IL)

( * ) Notice: Subject to any disclaimer, the term of this patent is extended or adjusted under 35 U.S.C. 154(b) by 303 days.

(21) Appl. No.: 16/884,090

(22) Filed: May 27, 2020

(65) Prior Publication Data

US 2020/0375918 A1 Dec. 3, 2020

Related U.S. Application Data

(60) Provisional application No. 62/853,574, filed on May 28, 2019.

(51) Int. Cl.

| | |
|---|---|
| A61K 31/05 | (2006.01) |
| A61P 27/02 | (2006.01) |
| A61K 47/44 | (2017.01) |
| A61K 31/167 | (2006.01) |
| A61K 9/00 | (2006.01) |
| A61K 9/06 | (2006.01) |

(52) U.S. Cl.
CPC ............ *A61K 31/05* (2013.01); *A61K 9/0014* (2013.01); *A61K 9/0048* (2013.01); *A61K 9/06* (2013.01); *A61K 31/167* (2013.01); *A61K 47/44* (2013.01); *A61P 27/02* (2018.01)

(58) Field of Classification Search
None
See application file for complete search history.

(56) References Cited

U.S. PATENT DOCUMENTS 9,549,906 B2 * 1/2017 Lynch .................. A61K 31/015

FOREIGN PATENT DOCUMENTS

WO WO 2016/153347 * 9/2016 ............. C07C 37/70

OTHER PUBLICATIONS

Nelson et al (Investigative Ophthalmology and Visual Science, 52(4):1930-1937, 2011) (Year: 2011).*
Perry (US Sensory Disorders, pp. 17-19, 2006) (Year: 2006).*
Pleyer et al (Ophthalmol Ther 2:55-72, 2013) (Year: 2013).*
Liu et al (ARVO Annual Meeting Abstract, 2005) (Year: 2005).*
Maher (Oman J Opthalmology 11:11-15, Jan.-Apr. 2018) (Year: 2018).*
Bezabh et al (Pharmaceutics 14:1587, 2022) (Year: 2022).*
Miller et al (Invest Ophthalmol Vis Sci 59:5904-5911, 2018) (Year: 2018).*
Indiana University. "CBD in marijuana may worsen glaucoma, raise eye pressure: Research in mice suggests over-the-counter substance could possess unknown side effects." ScienceDaily. ScienceDaily, Dec. 17, 2018 .<www.sciencedaily.com/releases/2018/12/181217151537.htm>—2 pages.
Tomida et al., "Effect of sublingual application of cannabinoids onintraocular pressure: a pilot study"; J. Glaucoma Oct. 2006;15(5):349-53.—1 page.
Valenti, "Is there a Risk of Blindness With CBD?" Poster American Public Health Association 2018 by IMMAD, LLC Impairment Measurement Marijuana and Driving—8 pages.
Kiger, "Eye Doctors Caution Against Using CBD as Glaucoma Remedy", https://www.aarp.org/health/drugs-supplements/info-2019/cbd-glaucoma.html#:~:text=But an organization of eye,pegged to Glaucoma Awareness Month; Jan. 24, 2019—6 pages.
Straiker (2019) What is currently known about cannabidiol and ocular pressure, Expert Review of Ophthalmology, 14:6, 259-261, DOI: 10.1080/17469899.2019.1698947—4 pages.
Baptist Eye Surgeons, "CBD and Glaucoma—Are They a Safe Combination?", https://www.baptisteye.com/warning-cbd-can-make-glaucoma-or-high-eye-pressure-worse/, Nov. 3, 2021; 11 pages.
Mosaed, "Cannabis, Glaucoma and Intraocular Pressure" Review of Ophthalmology, Jobson Medical Information LLC, published Apr. 10, 2022—10 pages.
Miller et al., "Delta9-Tetrahydrocannabinol and Cannabidiol Differentially Regulate Intraocular Pressure", Invest Ophthalmol Vis Sci. 2018;59:5904-5911. https://doi.org/10.1167/iovs.18-24838 (8 pages).

* cited by examiner

*Primary Examiner* — Craig D Ricci
(74) *Attorney, Agent, or Firm* — Roach Brown McCarthy & Gruber, P.C.; Kevin D. McCarthy

(57) ABSTRACT

Embodiments relate to a method for treatment of blepharitis in a patient in need thereof comprising administering to a subject in need thereof a pharmaceutical composition comprising a pharmaceutically effective amount of at least one cannabinoid, via the topical route. Optionally, the pharmaceutical composition is administered in combination with an additional agent selected from the group consisting of: an essential oil, a steroid, an antibiotic, an anti-parasitic, a disinfectant, an anesthetic, a terpene, a moisturizer and a vitamin.

17 Claims, No Drawings

COMPOSITIONS FOR THE TREATMENT OF BLEPHARITIS

CROSS REFERENCE TO RELATED APPLICATIONS

This application claims the benefit of U.S. provisional patent application No. 62/853,574, filed on May 28, 2019, the contents of which is incorporated by reference herein in its entirety.

FIELD

The present invention relates to topical pharmaceutical compositions for the treatment of blepharitis, and to methods for treatment of blepharitis, evaporative tear dysfunction and dry eye.

BACKGROUND

Blepharitis is one of the most common ocular conditions characterized by inflammation, scaling, reddening, and crusting of the eyelid. Blepharitis is a chronic condition with times of exacerbation or remission in the inflammatory process. Although blepharitis is not a sight-threatening condition in most cases, in some cases it can lead to corneal ulceration and corneal opacities or it can lead to permanent alterations of the eyelid margin, tear film stability and ocular surface state. The overall etiology may be bacterial overgrowth, inflammation or from congested meibomian oil glands. Other conditions may give rise to blepharitis, whether they be infectious or noninfectious, including, but not limited to, viral infections, *Demodex folliculorum*, or allergies.

Different variations of blepharitis can be classified as seborrheic, staphylococcal, mixed, posterior or meibomitis, meibomian gland dysfunction or parasitic. In a survey of US ophthalmologists and optometrists, 37% to 47% of patients seen by those surveyed had signs of blepharitis, which can affect all ages and ethnic groups. One single-center study of 90 patients with chronic blepharitis found that the average age of patients was 50 years old.

Treatment of blepharitis has been described in US Patent Application Publication 2019/0117563 and US Patent Application Publication 2017/0232024, both incorporated herein by reference.

SUMMARY

Described herein are methods for treatment of blepharitis comprising administering to a subject in need thereof, a pharmaceutical composition comprising a pharmaceutically effective amount of at least one cannabinoid.

The foregoing and other objects, features, and advantages will become more apparent from the following detailed description.

DETAILED DESCRIPTION

Unless otherwise noted, technical terms are used according to conventional usage. Definitions of common terms in pharmaceutical sciences can be found in Troy et al. Remington: The Science and Practice of Pharmacy. Published by Lippincott Williams & Wilkins, 2006. In case of conflict, the present specification, including explanations of terms, will control. In addition, all the materials, methods, and examples are illustrative and not intended to be limiting.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia and is used herein to indicate a non-limiting example. Thus, the abbreviation "e.g." is synonymous with the term "for example."

Definitions

Anesthetic: A drug administered to a part of a body to induce temporary loss of sensation in a part of the body.

Cannabinoid: A cannabinoid is a chemical compound that acts on cannabinoid receptors in cells in mammals, including in humans Cannabinoids can be manufactured synthetically or obtained from various parts of the genus *Cannabis*, for example, from the buds of species *Cannabis Sativa*. Cannabinoids from the cannabis plant are referred to as phytocannabinoids. Two preferred cannabinoids according to various embodiments, are (−)-trans-Δ□-tetrahydrocannabinol, and/or isomers thereof (THC) and cannabidiol (CBD). Alternatively, a cannabinoid may be in the form of cannabis extract. Alternatively, a cannabinoid may be in the form of a synthetic cannabinoid. Compositions described herein may comprise one cannabinoid or multiple cannabinoids, such as a combination of CBD and THC.

Combination: A treatment modality combining two or more treatments (therapies or agents). Combination therapy may involve administration of the two or more treatments at the same time, sequentially, or with a gap of time between the administrations. In combination therapy, although not always administered simultaneously, the biological effects of both of the drugs or treatments occur on the subject at relatively the same time. Combination therapy may involve two drugs or treatments in one dosage form or multiple drugs or treatments in separate dosage forms.

Essential Oil: an essential oil is a hydrophobic liquid containing volatile chemical compounds from plant origin.

Synergy: refers to a clinical observation wherein a combination of two treatments, such as cannabinoid therapy and an additional therapy, when administered in combination, provides more than additive effect of the individual therapies on their own.

DESCRIPTION OF EMBODIMENTS

Described herein, according to some embodiments, are compositions which can be easily applied to the eyelid and provide relief to patients suffering from blepharitis. Compositions, according to an embodiment, comprise at least one cannabinoid and a carrier.

Optionally, the cannabinoid is one of, or a combination of more than one of: tetrahydrocannabinol (THC), tetrahydrocannabinolic acid (THCA), cannabidiol (CBD), cannabidiolic acid (CBDA), cannabinol (CBN), cannabichromene (CBC), cannabigerol (CBG), cannabicyclol (CBL), cannabivarin (CBV), tetrahydrocannabivarin (THCV), cannadibivarin (CBDV), cannabichromevarin (CBCV), cannabigerovarin (CBGV), cannabigerol monomethyl ether (CBGM), cannabielsoin (CBE) and cannabicitran (CBT). Optionally, the cannabinoid is CBD.

Optionally, the composition comprises an oil extracted from a cannabis plant. Optionally, the oil is hemp oil or cannabis oil. A single cannabinoid or a plurality of cannabinoids may be present in the hemp oil or in the cannabis oil. Optionally, the cannabinoid is isolated or synthetically manufactured.

The compositions may comprise between 0.1% and 10% by weight of cannabinoid. Optionally the composition comprises between 0.5% and 2% by weight of cannabinoid.

Optionally, the carrier is an oil-based carrier, selected from the group consisting of: benzyl alcohol, cetyl alcohol, diglycol stearate, glyceryl monostearate, liquid paraffin, light liquid paraffin, white soft paraffin and petrolatum, or natural oils such as coconut oil, avocado oil, sesame oil, almond oil, olive oil, soy oil and cashew oil. Preferably, the carrier is petrolatum.

The composition, preferably, comprises 70% to 90% oil-based carrier. Optionally, the composition comprises 75% to 85% oil-based carrier.

In addition to a cannabinoid, the composition may comprise an additional active agent. According to an embodiment, the additional agent is selected from the group consisting of: an essential oil, a steroid, an antibiotic, an anti-parasitic, a disinfectant, an anesthetic, a terpene, a moisturizer, and a vitamin. The amounts of the additional agent in the composition may be from 0.01% to about 20% of the composition.

According to an embodiment, the essential oil is selected from the group consisting of: neem oil, tea tree oil, clove, cedarwood, lemon, and sweet orange. Optionally, the essential oil is present in an amount of 5% to 20%, preferably 10-15%. Preferably, the essential oil is tea tree oil.

According to an embodiment, the steroid is dexamethasone, loteprednol, or a pharmaceutically acceptable salt thereof. Optionally, the steroid is present in an amount between 0.01% and 2% of the composition.

According to an embodiment, the antibiotic is polymyxin b, neomycin, tobramycin, erythromycin, or doxycycline. Optionally, the antibiotic is present in an amount between 0.01% and 2% of the composition According to an embodiment, the anesthetic is selected from the group consisting of: lidocaine, amethocaine, proparacaine, tetracaine, and pharmaceutically acceptable salts thereof. Optionally, the anesthetic is present in the composition in an amount of between 0.2% and 3.5% by weight.

According to an embodiment, the vitamin is selected from the group consisting of vitamin A (250 UI/g), vitamin C (05%-5%), and vitamin E (0.5%-5%).

According to an embodiment, the terpene is terpinen-4-ol. The terpene may be present in an amount of 5% to 20%, preferably 10-15%. Optionally, the terpene is α-terpinene, γ-terpinene, α-terpineol, terpinolene, p-cimene, sabinene or α-pinene.

According to an embodiment, the composition comprises at least one pH modifying agent. The pH modifying agent may be selected from the group consisting of an acid, a base, and a buffer. The pH modifying agent may be added to modify the pH of the composition to a pH of 3.5-7.5 level. Preferably, the pH of the composition is 7.0 According to an embodiment, the disinfectant can be a hypochlorous acid (HOCl) (0.01%-0.02%).

According to an embodiment, the composition further comprises a moisturizer. Optionally, the moisture is selected from the group consisting of glycerin, squalene, and shea butter. Optionally aloe vera can be added as skin moisturizer, repair damaged skin and reduce puffiness around the eye margins. Moisturizers may be included in the composition in amounts of between 5 and 10% by weight.

According to an embodiment, the composition comprises at least one more inactive excipient selected from the group consisting of: a stabilizer, an emulsifier, and a thickener.

Compositions according to an embodiment are designed to be applied to a surface of an eyelid of a patient in need thereof, and to remain on the surface of the eyelid for an extended period, preferably, at least 30 minutes. According to an embodiment, the composition is in the form of an ointment, a cream, a lotion, a gel, or a foam.

When the composition is a cream or a paste, its viscosity at 25° C. is preferably between 50,000 and 64,000 centipoise (cps). When the composition is a lotion, its viscosity at 25° C. is preferably between 700 and 10,000 cps. When the composition is a gel, its viscosity at 25° C. is preferably between 3,000 and 5,000 cps.

Some embodiments relate to methods for treatment of blepharitis comprising administering to a patient in need thereof, via the topical route, a pharmaceutical composition comprising an effective amount of a cannabinoid. Optionally the cannabinoid is THC. Optionally, the cannabinoid is CBD. The blepharitis may be seborrheic, staphylococcal, mixed, posterior, meibomitis, Meibomian Gland Dysfunction or parasitic demodex blepharitis. Optionally, the method may comprise administering to a patient, in combination, an additional agent selected from the group consisting of: an essential oil, a steroid, an antibiotic, an anesthetic, a terpene, and a vitamin. The additional agent may be administered in the same composition, or in a separate composition.

The amount of composition administered, per administration may be between 0.1 g and 0.3 g per eyelid. The administration may be once daily, twice daily, three times daily, or four times daily. Optionally, the treatment continues for 30 days. When the composition comprises an anesthetic agent, the composition is preferably administered up to twice daily.

According to an embodiment, the composition is applied to the eyelid margin and eyelashes. Optionally, the composition is applied, and then the subject scrubs the eyelid margin, eyelashes and eyelash roots with the composition, optionally using a cloth, a disposable wipe, a sponge, a brush or a cotton-tipped applicator.

The composition may be applied on a daily basis for 30 days.

Further provided herein are methods for treatment of blepharitis comprising administering to a patient in need thereof, a cannabinoid, in combination with an additional active agent, in amounts which show a synergistic effect of the combination treatment relative to the cannabinoid alone and additional active agent alone.

Additional embodiments relate to a kit comprising a composition as described herein, comprising a cannabinoid for administration via the topical route for the treatment of blepharitis, and an applicator. The applicator may be a cloth, a disposable wipe, a sponge, a brush or a cotton tipped applicator. The applicator may be packaged with the composition, and packaged in a sealed package to maintain sterility of the applicator. The applicator may be permeated with the composition, to provide ease of administration of the composition to the affected area such as the eyelid of a patient suffering from blepharitis. The kit, optionally, comprises written instructions which direct a user to apply the composition, using the applicator to the eyelid margin, eyelashes, and eyelash roots.

EXAMPLES

Example 1A

A composition is prepared using the ingredients listed in table 1:

TABLE 1

| Ingredient | Function | Amount (Weight/Percent) |
|---|---|---|
| White Petrolatum - Mineral Oil | Humectant | 79.5 |
| Hemp Oil containing 10% CBD | Anti-Inflammatory | 5 |
| Tea Tree Oil (Melaleuca Oil) | Anti-Parasitic | 12 |
| Lidocaine HCl | Anesthetic | 3.5 |

The composition is prepared by introducing the white petrolatum into a vessel, then adding the other ingredients while mixing, keeping the mixture at 25° C. or below.

The resultant formulation is expected to be stable for 8 months at room temperature below 25 Celsius and the CBD level is 0.45%-0.55%. The amount of tea tree oil is between 11%-12% and the amount of lidocaine is 3.5%.

Example 1B

A composition is prepared using the ingredients listed in table 2 below.

TABLE 2

| Ingredient | Function | Amount (Weight/Percent) |
|---|---|---|
| White Petrolatum - Mineral Oil | Humectant | 90 |
| Hemp Oil 10% CBD | Anti-Inflammatory | 5 |
| Tea Tree Oil (Melaleuca Oil) | Anti-Parasitic | 5 |

The composition is prepared using the same process described in Example 1A. The resultant formulation is expected to be stable for 8 months at room temperature below 25 Celsius and to have a resultant CBD level of 0.45%-0.55%, tea tree oil between 3%-5%.

Example 1C

A composition is prepared using the ingredients listed in table 3.

TABLE 3

| Ingredient | Function | Amount (Weight/Percent) |
|---|---|---|
| White Petrolatum - Mineral Oil | Humectant | 79.5 |
| Full Spectrum CBD Oil | Anti-Inflammatory | 5 |
| Tea Tree Oil (Melaleuca Oil) | Anti-Parasitic | 12 |
| Lidocaine Hcl | Anesthetic | 3.5 |

The composition is prepared using the same process described in Example 1A. The resultant formulation is expected to be stable for 8 months at room temperature below 25° C. The resultant formulation includes CBD level is 0.45%-0.55%, trace amounts of THC, the amount of tea tree oil is between 11%-12% and the amount of local anesthetic is at 3.5%.

Example 1D

A composition is prepared using the ingredients listed in table 4.

TABLE 4

| Ingredient | Function | Amount (Weight/Percent) |
|---|---|---|
| White Petrolatum - Mineral Oil | Humectant | 87 |
| CBD Isolate | Anti-Inflammatory | 0.5 |
| Terpinen-4-ol | Anti-Parasitic | 9 |
| Lidocaine Hcl | Anesthetic | 3.5 |

The composition is prepared using the same process described in Example 1A. The resultant formulation is stable for 8 months and the CBD level is 0.45%-0.55%. The amount of terpinen4-ol is between 9%-10% and the amount of lidocaine is 3.5%.

Example 2: Trial of Cannabinoid Composition for Treatment of Patients Suffering from Blepharitis Subjects are screened and are found to be have dry eye as a result of meibomian gland dysfunction (MGD), resulting from blepharitis. Subjects, aged 18 to 80, are included in the study if diagnosed with dry eye due to MGD resulting from blepharitis. Subjects having tear breakup time of less than or equal to 7 seconds, and having a score greater than 23 on the Ocular Surface Disease Index are included.

Subjects are provided with composition comprising a cannabinoid and a terpene, as prepared in Example 1B, and administer twice daily for 30 days.

Subjects treated with the cannabinoid-containing compositions may show improvement of dry eye disease due to MGD as evaluated by tear breakup time test at the end of the 30 days of administration.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for treatment of blepharitis comprising topically administering to a surface of the eyelid of a subject in need thereof a composition comprising a pharmaceutically acceptable amount of cannabinoid, wherein the cannabinoid includes at least one member selected from the group consisting of cannabidiol (CBD), cannabigerol (CBG), and cannabigerovarin (CBGV), and wherein the composition does not comprise any additional cannabinoids.

2. The method according to claim 1 wherein the cannabinoid is CBD.

3. The method according to claim 1 wherein the composition comprises an oil based carrier.

4. The method according to claim 3 wherein the composition comprises between 70% and 90% oil based carrier.

5. The method according to claim 1 wherein the pharmaceutical composition is administered in combination with an additional agent selected from the group consisting of: an essential oil, a steroid, an antibiotic, an anti-parasitic, a disinfectant, an anesthetic, a terpene, a moisturizer and a vitamin.

6. The method according to claim 5 wherein the essential oil is selected from the group consisting of: neem oil, tea tree oil, clove oil, cedarwood oil, lemon oil, and sweet orange oil.

7. The method according to claim 5 wherein the steroid is dexamethasone, loteprednol, or a pharmaceutically acceptable salt of the steroid.

8. The method according to claim 5 wherein the antibiotic is polymyxin b, neomycin, tobramycin, erythromycin, or doxycycline.

9. The method according to claim 5 wherein the anesthetic is selected from the group consisting of: lidocaine, amethocaine, proparacaine, tetracaine, and pharmaceutically acceptable salts thereof.

10. The method according to claim 5 wherein the vitamin is selected from the group consisting of vitamin A, vitamin C, and vitamin E.

11. The method according to claim 1 wherein the composition remains on the surface of the eyelid for at least 30 minutes.

12. The method according to claim 1 wherein the composition is in the form of an ointment, a cream, a lotion, a gel, or a foam.

13. The method according to claim 1 wherein the composition comprises between 0.1% and 10% by weight of cannabinoid.

14. The method according to claim 1 wherein the composition is applied to the eyelid margin and eyelashes.

15. The method according to claim 14 wherein the composition is applied in an amount of between 0.1 g and 0.3 g per eyelid.

16. The method according to claim 1 wherein the composition is applied between twice and four times daily.

17. The method according to claim 1 wherein the composition is applied using a cloth, a disposable wipe, a sponge, a brush or a cotton-tipped applicator.

* * * * *